(12) United States Patent  
Nakamura

(10) Patent No.: US 6,257,757 B1  
(45) Date of Patent: Jul. 10, 2001

(54) THERMAL ANALYSIS APPARATUS

(75) Inventor: Nobutaka Nakamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/313,117

(22) Filed: May 17, 1999

(30) Foreign Application Priority Data

May 18, 1998 (JP) .................................................. 10-135640

(51) Int. Cl.$^7$ ........................... G01N 25/00; G01N 25/16
(52) U.S. Cl. ................................ 374/14; 374/10; 374/12; 374/31; 374/43; 374/45
(58) Field of Search ..................... 374/10, 12, 31, 374/43, 45, 14, 55, 56

(56) References Cited

U.S. PATENT DOCUMENTS

| | | | | |
|---|---|---|---|---|
| 3,298,220 | * | 1/1967 | Stone et al. ............................. | 374/13 |
| 4,964,734 | * | 10/1990 | Yoshida et al. ......................... | 374/14 |
| 5,588,746 | * | 12/1996 | Minobe et al. ......................... | 374/10 |
| 5,669,554 | * | 9/1997 | Nakamura et al. ..................... | 374/14 |
| 5,826,983 | * | 10/1998 | Nakamura et al. ..................... | 374/14 |
| 5,983,711 | * | 11/1999 | Pappas et al. .......................... | 374/14 |
| 6,095,690 | * | 8/2000 | Barata .................................... | 374/43 |
| 6,146,012 | * | 11/2000 | Nakamura et al. ..................... | 374/10 |
| 6,146,013 | * | 11/2000 | Huetter et al. ......................... | 374/46 |
| 6,170,984 | * | 1/2001 | Schawe et al. ......................... | 374/10 |

FOREIGN PATENT DOCUMENTS

| | | | |
|---|---|---|---|
| 3717712A1 | * | 12/1988 | (DE) . |
| 404064047 | * | 2/1992 | (JP) ....................................... 374/14 |
| 404164241 | * | 6/1992 | (JP) ....................................... 374/31 |
| 404204364 | * | 7/1992 | (JP) ....................................... 374/31 |
| 0821964 | * | 4/1981 | (SU) ...................................... 374/31 |

* cited by examiner

Primary Examiner—G. Bradley Bennett  
Assistant Examiner—Gail Verbitsky  
(74) Attorney, Agent, or Firm—Adams & Wilks

(57) ABSTRACT

A gas-tight container such as a glove box maintains a sample under a controlled atmosphere and has a sample chamber formed in a convex portion thereof. The temperature is controlled in the sample chamber by an externally disposed heater. A detector such as a weight detector is disposed in the gas-tight container and has a sample holder for holding a sample under analysis. The detector is movably supported by a movement mechanism so that the sample holder is movable between a first position at which a sample disposed on the sample holder is disposed within the sample chamber and a second position at which a sample disposed on the sample holder is disposed outside the sample chamber, such that the mounting of a sample on the sample holder may be accomplished while the sample holder is disposed outside the sample chamber and a thermal analysis of the sample may be performed while the sample is disposed inside the sample chamber. Gas inlet and outlet ports are provided to form a stream of purge gas to continually replace the atmosphere in the gas-tight chamber and the sample chamber, and the gas produced by the sample during analysis thereof is discharged together with the purge gas through a gas discharge port provided at a tip of the sample chamber.

36 Claims, 1 Drawing Sheet

THERMAL ANALYSIS APPARATUS

BACKGROUND OF THE INVENTION

The present invention relates to a thermal analysis apparatus for measuring a signal representative of a change physical or chemical property of a sample as a function of temperature or time. More particularly, the invention relates to an thermal analysis apparatus which enables the atmospheric conditions surrounding a sample to be controlled throughout, before and after measurement, which has conventionally been difficult.

Thermal analysis is an effective means for examining as to how a material property is changed by time or temperature. The thermal analysis apparatuses generally known include, as typical examples, a differential scanning calorimeter (DSC), differential thermal analysis apparatus (DTA), thermogravimetric analysis apparatus (TG), thermomechanical analysis apparatus (TMA) and so on. These apparatuses have respective objects to measure sample enthalpy change, differential heat (qualitative enthalpy change), weight change and dimensional change as a function of temperature or time. In thermal analysis, a sample is varied in accordance with a programmed temperature function in order to measure simultaneously a signal from a converter for property value measurement and a temperature signal. The data of a combination of the property signal and temperature signal thus measured is usually represented on a temperature-property two dimensional coordinate. At this time, if a temperature program used differs, a different thermal analysis curve is generally obtained. Thus, the temperature program is one of the most important parameters representative of measuring conditions.

Also, heating up carbon in air produces an oxidizing decomposition reaction whereas a similar experiment if conducted in nitrogen does not cause a reaction. As may be inferred from this example, it is often the case that changing the atmosphere around a sample provides substantially different thermal analytic result. That is, in thermal analysis the atmosphere for a sample is also an important parameter to represent measurement conditions.

Most of the thermal analysis apparatuses presently marketed are structured such that a temperature program as mentioned above or measuring condition parameter such as atmosphere can be controllably set in order to secure reliability in measurement result.

Meanwhile, there is also an attempt to accommodate entirely a commercially available thermal analysis apparatus within a gas tight chamber for the purpose of desirably setting sample atmosphere throughout, before and after measurement.

In the commercially available thermal analysis apparatus, measurement can be made on sample atmosphere during measurement. However, it has been impossible or difficult to set for sample atmosphere upon placing a sample in the thermal analysis apparatus before measurement.

There are cases that a sample, as it may be, if merely allowed to stand in air at room temperature be subjected to oxidation or deliquescence. If thermal analysis is conducted on such a ample, a analytical result is changed by the atmosphere in an entire laboratory in addition to the atmosphere within the thermal analysis apparatus. Therefore it is clearly insufficient that sample atmosphere can be set only after placing a sample in the apparatus, from a viewpoint of securing reliability in measurement result.

On the other hand, the method of accommodating the entire apparatus in a gas tight chamber has an advantage in that it provides the capability of setting sample atmosphere before measurement. However, the chamber includes therein the heating oven so that heat is filled within the chamber and output signals of the apparatus are liable to become out of order. There are also problems in that the chamber is contaminated on the inside due to the discharge of a gas produced by sample decomposition, the gas if to be discharged from the sample chamber to a chamber outside makes piping complicate resulting in difficulty in keeping temperature of the piping system and hence incapability of analyzing the gas, and so on.

SUMMARY OF THE INVENTION

In order solve the above problems, the present invention employs a gas tight chamber in a glove box form in which an internal atmosphere can be replaced and an internal machine can be manually operated through use of a glove. The gas tight chamber has one wall surface on which an outwardly convex formed sample chamber is provided and the temperature within the sample chamber is controlled by a heating oven fixed outside the sample chamber. The gas tight chamber has at its interior a detector to measure a property of a sample, wherein the detector can be moved by a movement mechanism. A gas can be sent through a gas introducing port to an inside of the gas tight chamber so that the atmosphere within the gas tight chamber is replaced and at the same time a gas produced from the sample is discharged togehter therewith through a gas discharge port provided at a front end of the sample chamber.

In a preferred embodiment, an operator transports a sample into the gas tight chamber prior to measurement and control of an atmosphere within the gas tight chamber is effected by gas replacement. Then the operator moves the detector through use of the glove and retracts a sample hold section from the sample chamber. In this state the sample is rested on a sample holder provided at a tip of the detector and then the detector is moved to accommodate the sample within the sample chamber. Thereafter, similarly to the usual thermal analysis, a temperature program is set and various information concerning the sample are inputted, to start a measurement. In this series of processes, the sample is at all times within the gas tight chamber under a controlled atmosphere throughout before and after the measurement. Accordingly, there is no fear of oxidation deliquescence or other quality changes to occur.

DETAILED DESCRIPTION OF THE INVENTION

Figure 1:
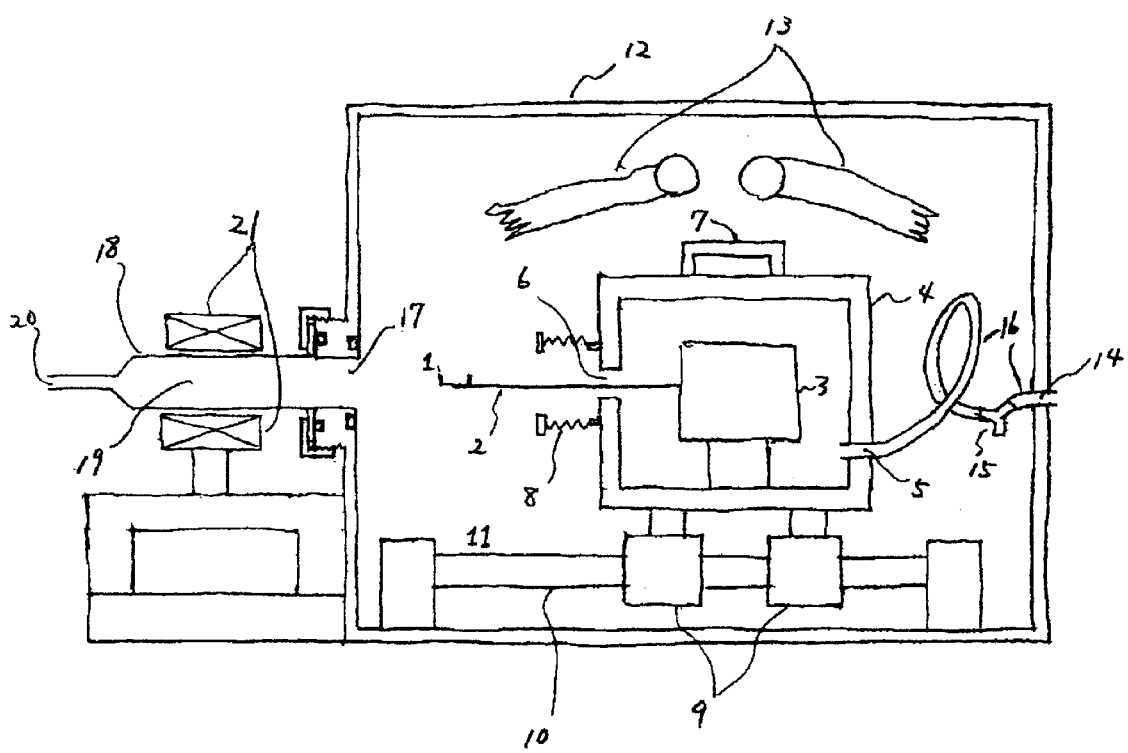
FIG. 1 is a block diagram of a TG measuring apparatus as one embodiment of the present invention.

Hereinunder an embodiment of the present invention will be explained in detail.

FIG. 1 shows an apparatus wherein the present invention is applied for thermogravimetric measurement (TG). In FIG. 1, a reference numeral 1 is a sample holder or sample holding section for placing thereon a sample to be measured. A sample (not shown) disposed on the sample holder 1 has its weight which is to be detected by a weight detector 3 connected through a sintered alumina beam 2. Also, the temperature of the sample is detected by a thermocouple (not shown) built into the beam 2 and having a tip welded to a bottom surface of the sample holder 1.

The weight detector 3 is fixed at the inside of a detector case 4. Although the detector case 4 forms therein an almost closed space the detector case has 4 has, two opening ports including a port for introducing a purge gas purge gas introducing port 5, and a beam passing window 6. A grip or handle 7 is fixed on an upper portion of the detector case 4. Incidentally, the beam 2 extending from the weight detector 3 fixed to the detector case 4 penetrates through the beam passing window 6. At the outside of the beam passing window 6, a sealing member in the form of a tubular bellows 8 is provided in a form enveloping the beam 2. The bellows 8 possesses extendibility and contractility in a lengthwise direction and at a same time the gas tightness between the bellows interior and exterior.

A movement mechanism 11 having main parts including a bearing 9 and a guide rod 10 is formed under the detector case 4, an can move the detector case 4 by sliding the bearing 9 fixed to the detector case 4 along the guide rod 10. Because the guide rod 10 is provided in direction matching the longitudinal or lengthwise direction of the beam 2, the detector case 4 and the weight detector 3 fixed therein can move along the lengthwise direction of the beam 2.

A gas tight container in the form of a glove box 12 is structured to accommodate therein the detector case 4 and is the movement mechanism 11, and provided with one set of gloves 13 so that an operator can operate inside the glove box 12. Incidentally, the glove box 12 is provided with a purge gas introducing port or inlet port 14 for introducing a purge gas into the glove box in order to replace the inside atmosphere. The purge gas introducing port 14 is connected to one end of a three-way joint 15 with a pipe 16. The three-way joint 15 has the other one end thereof connected to the gas introducing port 5 through the pipe 16 for introducing the purge gas into the detector case. Also, the remaining end of the three-way joint 15 is open to an interior of the glove box 12 so that the atmosphere is replaced by introducing a purge gas to the interior of the glove box 12.

On an outer side of a sample section communication window 17, a fastener tube 18 formed of sintered alumina in a cylindrical shape is fixed through an O ring for keeping tightness, wherein the fastener tube 18 has an internal space functioning as a sample chamber 19. As shown in FIG 1, the 12 fastener tube 18 comprises a convex-shaped portion or extension of the container 12 is provided at its tip with a discharge or outlet port 20 restricted to a small. Also, the fastener tube 18 has a side surface wound in a doughnut form by a heating oven 21. The heating oven 21 heats up the sample chamber 19 through the fastener tube 18.

Next, the operation of the present apparatus will be explained.

First, the operator operates the grip or handle 7 through the glove 13 and moves the detector case 4 rightward in FIG. 1 to a stop position where it is fixed in position. Also, a gas adapted for a measurement object, such as nitrogen or argon, is introduced through a detector into-case purge gas introducing port 15 and the pipe 16, to conduct gas replacement inside the glove box 12 and the detector case 4. Incidentally, because at this time the efficiency of gas replacement can be raised by once reducing the pressure inside the glove box 12, a pressure reducing means (not shown) is appropriately usable.

The operator puts a sample previously transported to the inside of the glove box 12 into a vessel (not shown) through the glove 13 and places the vessel containing the sample on the sample holder 1 using tweezers. Next, the grip 7 is operated to move the detector case 4 leftward in FIG. 1 to a stop position. At this time, the sample holder 1 is set such that its position comes to a center portion of the sample chamber 19. The interior space of the detector case 4 and the sample chamber 19 are connected through the bellows 8 and the sample section communication window 17 forming an almost closed space disconnected from the interior space of the globe box 12 by the sealing action of the bellows 8. The purge gas introduced through the into-box purge gas introducing port 14 is introduced to the inside of the detector case 4 via the three-way joint 15, pipe 16 and into-case purge gas introducing port 5, and then through the beam passing window 6 and sample section communication window 17 to the sample chamber 19 where it becomes together with a decomposition product from the sample, being discharged through the discharge port 20 to the outside. Incidentally, at this time the gas flowing from the released end of the three-way joint 15 into the inside of the glove box 12 has no exit and spontaneously stops due to a relation to pressure. Accordingly, the total amount of the purge gas introduced is used for gas replacement of the sample chamber 19.

The operation after this is similar to the case of usual thermal analysis. That is, the operator sets a temperature program condition to a thermal analysis controller (not shown) and inputs a sample name and other information, then starting a measurement.

Incidentally, if a mass analyzer or infrared spectrometer is connected to the discharge port 20 in the present embodiment structure through a heat insulation tube, it is possible to conduct analysis on a produced gas with a simplicity equivalent to that of the conventional thermal analysis apparatus.

Although explanation was made in the present embodiment of a method of manually placement of a sample, easy sample automatic placement is possible by adding an automatic transport mechanism to an apparatus using the structure of the present invention. In this case, easily realized is atmosphere control throughout, before and after measurement in a thermal analysis measurement using the automatic transport unction.

As stated above, according to the present invention, it is possible to control an atmosphere throughout, before and after measurement regardless of whether sample attachment to the detector is conducted manually or automatically. Accordingly, it is possible to obtain an effect that, in a thermal analysis on a readily-oxidative sample or deliquescent sample, sample oxidation or deliquescence not only in measurement but also prior to measurement.

Also, according to the present invention, a heat oven can be arranged outside the box differently from a method in which the entire thermal analysis apparatus is placed in a glove box. Accordingly, there is no heat filled within the box and hence no problem that the detector goes out of order due to affection of heat.

Further, according to the structure of the present invention, the sample decomposition gas is not discharged to the inside of the gas tight chamber in a glove box form and accordingly the interior of the gas tight chamber is free of contamination. The total amount is discharged to the outside through the discharge port. Consequently, an effect that a composite analysis with a produced gas analysis is realized is provided by connecting a mass analyzer or infrared spectrometer downstream of the discharge port.

What is claimed is:

1. A thermal analysis apparatus comprising: a gas-tight container defining an internal sample-containing area for maintaining a sample under a controlled atmosphere; gas inlet and outlet ports formed in the gas-tight container for charging and discharging a gas into and out of the sample-containing area to control the atmosphere therein; a sample chamber having a convex-shaped portion formed in the gas-tight container; a heating oven provided outside the sample chamber for heating the sample chamber; a detector provided inside the gas-tight container for detecting a change in a physical property of the sample during an analysis of the sample; a sample holding section having a sample holder provided on the detector; and a movement mechanism arranged within the gas-tight container for movably supporting the detector within the gas-tight container so that the sample holding section is movable between a first position at which a sample disposed on the sample holder is located within the sample chamber and a second position at which a sample disposed on the sample holder is not located within the sample chamber so that the sample may be placed on the sample holder when the sample holder is outside the sample chamber, and thermal analysis may be conducted on the sample by temperature control with the heating oven and detection with the detector when the sample holder is inside the sample chamber; whereby the atmosphere surrounding the sample can be controlled throughout, before and after measurement while the sample is disposed within the gas-tight container.

2. A thermal analysis apparatus comprising: a gas-tight container defining an internal sample-containing area for maintaining a sample under a controlled atmosphere; gas inlet and outlet ports formed in the container for charging and discharging a gas into and out of the sample-containing area to control the atmosphere therein; a sample chamber having a convex-shaped portion of the gas-tight container; a heating oven provided outside the sample chamber for heating the sample chamber; a detector provided inside the gas-tight container for detecting a change in a physical property of the sample during an analysis of the sample; a sample holding section having a sample holder provided on the detector; a detector case disposed inside the gas-tight container to fix the detector therein; and a movement mechanism arranged within the gas-tight container for movably supporting the detector case within the gas-tight container so that the sample holding section provided on the detector is movable between a first position at which a sample disposed on the sample holder is located within the sample chamber and a second position at which a sample disposed on the sample holder is not located within the sample chamber so that the sample may be sample placed on the sample holder when the sample holder is outside the sample chamber, and thermal analysis may be conducted on the sample by temperature control with the heating oven and detection with the detector when the sample holder is inside the sample chamber; whereby the detector case and the sample chamber are maintained in a closed space within the gas-tight container and the atmosphere surrounding the sample can be controlled throughout, before and after measurement while the sample is disposed within the gas-tight container.

3. A thermal analysis apparatus as recited in claim 2; wherein the gas-tight container comprises a glove box having an opening through which a glove extends; a peripheral edge of the glove through which an operator's hand may be inserted being attached to the glove box to form a gas-tight seal, so as to enable manual manipulation of a sample within the glove box and operation of internal components disposed in the glove box through use of the glove.

4. A thermal analysis apparatus according to claim 1; further comprising a detector case disposed inside the gas-tight container to fix the detector therein, the detector case being supported by the movement mechanism such that movement of the sample holding section is effected by movement of the detector case between the first and second positions, whereby the detector case and the sample chamber are maintained in an isolated space within the gas-tight container.

5. A thermal analysis apparatus according to claim 4; wherein the gas-tight container comprises a glove box having an opening through which a glove extends, an opening of the glove being attached to the glove box to form a gas-tight seal, so as to enable manual manipulation of a sample within the glove box and operation of internal components disposed in the glove box through use of the glove.

6. A thermal analysis apparatus according to claim 5; wherein the detector case includes a handle disposed so that the detector case may be used to move the sample holding section between the first and second positions via the movement mechanism by use of the handle.

7. A thermal analysis apparatus according to claim 5; further comprising means for conveying inlet gas from the gas inlet port to the detector case.

8. A thermal analysis apparatus according to claim 4; further comprising a sealing member attached to one of the gas-tight container and the detector case for creating a seal between the detector case and the sample chamber when the sample holding section is in the first position.

9. A thermal analysis apparatus according to claim 1; wherein the detector comprises a weight detector for detecting a weight variation of the sample with respect to temperature variation and time.

10. A thermal analysis apparatus according to claim 1; wherein the sample holding section comprises a beam having a first end connected to the detector and a second end connected to the sample holder on which the sample is disposed.

11. A thermal analysis apparatus according to claim 1; further comprising a thermocouple connected to the sample holder for detecting the temperature of the sample.

12. A thermal analysis apparatus according to claim 1; wherein a gas outlet port is formed in the sample chamber for discharging gas.

13. A thermal analysis apparatus according to claim 2; wherein the detector case includes a handle disposed so that the detector case may be used to move the sample holding section between the first and second positions via the movement mechanism by use of the handle.

14. A thermal analysis apparatus according to claim 2; further comprising means for conveying inlet gas from the gas inlet port to the detector case.

15. A thermal analysis apparatus according to claim 2; further comprising a sealing member attached to one of the gas-tight container and the detector case for creating a seal between the detector case and the sample chamber when the sample holding section is in the first position.

16. A thermal analysis apparatus according to claim 2; wherein the detector comprises a weight detector for detecting a weight variation of the sample with respect to temperature variation and time.

17. A thermal analysis apparatus according to claim 2; wherein the sample holding section comprises a beam having a first end connected to the detector and a second end connected to the sample holder on which the sample is disposed.

18. A thermal analysis apparatus according to claim 2; further comprising a thermocouple connected to the sample holder for detecting the temperature of the sample.

19. A thermal analysis apparatus according to claim 2; wherein a gas outlet port is formed in the sample chamber for discharging gas.

20. A measurement apparatus comprising: a gas-tight container defining an internal sample-containing area for maintaining a sample under a controlled atmosphere; a sample chamber disposed in a portion of the container; a detector provided inside the container for detecting a change in a physical property of the sample during an analysis of the sample; a sample holder for holding the sample; and a movement mechanism arranged within the gas-tight container for moving the sample holder within the container so that a sample disposed on the sample holder is movable between a first position at which the sample is disposed within the sample chamber and a second position at which the sample is not disposed within the sample chamber, so that the sample may be mounted to the sample holder when the sample holder is disposed outside the sample chamber, and a measurement may be conducted on the sample when the sample is disposed inside the sample chamber; whereby the atmosphere surrounding the sample can be controlled throughout, before and after measurement while the sample is disposed within the controlled atmosphere of the container.

21. A measurement apparatus according to claim 20; further comprising gas inlet and outlet ports formed in the gas-tight container for charging and discharging a gas in the sample-containing area to control the atmosphere therein.

22. A measurement apparatus according to claim 20; further comprising a heater disposed outside the sample chamber for heating the sample chamber.

23. A measurement apparatus according to claim 20; wherein the gas-tight container has inlet and outlet ports for charging and discharging a gas into and out of the sample-containing area.

24. A measurement apparatus according to claim 20; wherein the sample chamber is formed in a convex-shaped portion of the container.

25. A measurement apparatus according to claim 20; wherein the detector comprises a weight detector for detecting a variation in weight of the sample under analysis.

26. A measurement apparatus according to claim 20; wherein the sample holder is connected to the detector and the detector is movably supported by the movement mechanism so that the detector and the sample holder are movable as a unit between the first and second positions of the sample holder.

27. A measurement apparatus according to claim 20; wherein the container comprises a glove box.

28. A measurement apparatus according to claim 20; further comprising a detector case disposed inside the container to fix the detector therein, the sample holder being connected to the detector and the detector case being movably supported by the movement mechanism such that movement of the sample holder between the first and second positions is effected by movement of the detector case, whereby the detector and sample chamber may be maintained in an isolated space within the container and the atmosphere surrounding the sample can be controlled throughout, before and after measurement while the sample is disposed within the container.

29. A measurement apparatus according to claim 28; wherein the container comprises a glove box having an opening through which a glove extends, an opening of the glove being attached to the glove box to form a gas-tight seal, so as to enable manual manipulation of the sample within the glove box and operation of internal components disposed in the glove box through use of the glove.

30. A measurement apparatus according to claim 28; wherein the detector case includes a handle to enable manipulation of the detector case using the handle.

31. A measurement apparatus according to claim 28; further comprising a gas inlet port and a gas outlet port for charging and discharging a gas into and out of the container; and means for conveying inlet gas from the gas inlet port to the detector case.

32. A measurement apparatus according to claim 28; further comprising a sealing member attached to one of the gas-tight container and the detector case for creating a seal, between the detector case and the sample chamber when the sample holder is in the first position.

33. A measurement apparatus according to claim 20; wherein the detector comprises a weight detector for detecting a weight variation of the sample with respect to temperature variation and time.

34. A measurement apparatus according to claim 20; wherein the sample holder comprises a beam having a first end connected to the detector and a second end having a portion on which the sample may be disposed.

35. A measurement apparatus according to claim 20; further comprising a thermocouple connected to the sample holder for detecting the temperature of the sample.

36. A measurement apparatus according to claim 20; wherein a gas outlet port is formed in the sample chamber for discharging gas from the sample chamber.

* * * * *